United States Patent [19]

Hoffman, Jr. et al.

[11] Patent Number: 5,308,854
[45] Date of Patent: May 3, 1994

[54] INHIBITORS OF HIV REVERSE TRANSCRIPTASE

[75] Inventors: Jacob M. Hoffman, Jr., North Wales; Walfred S. Saari, Lansdale; Clarence S. Rooney, Worcester; John S. Wai, Lansdale, all of Pa.

[73] Assignee: Merck & Co., Inc., Rahway, N.J.

[21] Appl. No.: 971,691

[22] Filed: Nov. 4, 1992

Related U.S. Application Data

[63] Continuation of Ser. No. 799,915, Nov. 26, 1991, abandoned, which is a continuation of Ser. No. 539,681, Jun. 18, 1990, abandoned.

[51] Int. Cl.$^5$ .................... A61K 31/44; C07D 413/12
[52] U.S. Cl. .................................. 514/338; 546/270
[58] Field of Search ....................... 514/338; 546/270

[56] References Cited

U.S. PATENT DOCUMENTS

| | | | |
|---|---|---|---|
| 3,654,291 | 4/1972 | Witzel | 546/297 |
| 3,721,676 | 3/1973 | Witzel | 546/297 |
| 3,846,553 | 11/1974 | Shen | 514/345 |
| 3,853,896 | 12/1974 | Pessolano | 546/300 |
| 3,853,897 | 12/1974 | Witzel | 546/297 |
| 4,255,428 | 3/1981 | Brown | 514/272 |
| 4,461,901 | 7/1984 | Potoski | 546/270 |
| 4,839,371 | 6/1989 | Kouse et al. | 546/301 |

FOREIGN PATENT DOCUMENTS

| | | |
|---|---|---|
| 061774 | 10/1982 | European Pat. Off. |
| 373423 | 6/1990 | European Pat. Off. |
| 394553 | 10/1990 | European Pat. Off. |
| 0462808 | 12/1991 | European Pat. Off. |
| 89/8357 | 11/1989 | South Africa |

OTHER PUBLICATIONS

Zeffren et al. The Study of Enzyme Mechanism 1974 p. 87.
Wade Jr. Organic Chemistry 1987 Prentice-Hall Inc. p. 349.
Debyser, Z. et al. Proc. Natl. Acad. Sci. 88, 1451 (1991).
Ratner, L. et al., "Complete Nucleotide Sequence of the AIDS Virus, HTLV-III," Nature 313, 278 (1985).
Toh, H. et al., "Close Structural Resemblance . . . ," EMBO J 4, 1267 (1985).
Power, M. D. et al., "Nucleotide Sequence of SRV-1 . . . ," Science 231, 1567 (1986).
Pearl, L. H. et al., "A Structural Model of Retroviral Proteases," Nature 329, 351 (1987).
Brownstein, S. K., "Reaction of Nitroacetamide with Hypobromite," J. Org. Chem. 23, 113 (1958).
Okafor, C. O. et al.,". . . Analogues of . . . 2,3,6-Triazaphenothiazine . . . ," J. Heterocyclic Chem. 20, 199 (1983) (Okafor I).
Okafor, C. O., ". . . New Chemistry of Azaphenothiazine . . . ," J. Org. Chem. 47, 592 (1982) (Okafor II).
Paine, J. B.,". . . Synthesis of Nicotinate Esters . . . ," J. Heterocyclic Chem. 24, 351 (1987).
Baldwin, J. J. et al., "Synthesis of . . . 2-Halonicotinic Acid Derivatives," J. Org. Chem. 43, 2529 (1978).
Fauci, A. S., "Current issues in developing a strategy for dealing with AIDS," Proc. Natl. Acad. Sci. 83, 9278 (1986).
Baum, et al., "AIDS Vaccine . . .,"C&EN, pp. 7–14 (Jul. 16, 1990).
Sandstrom, E., "Antiviral Therapy," Drugs 38(3), 417(1989) (Sandstrom I).
Sandstrom, E. G. et al., "Antiviral Therapy in AIDS . . .," Drugs 34, 372 (1987) (Sandstrom II).
CA 115: 126401t, p. 24 (Sep. 30, 1991).
Waldholz, M., "Glaxo . . . Begins . . . Testing of AIDS Drug . . . ," The Wall Street Journal, p. B4 (Jul. 30, 1991).
Goldman, M. E. et al., "Pyridinone derivatives: Specific HIV-1 reverse transcriptase inhibitors . . . ," Proc. Natl. Acad. Sci. 88, 6863(1991).

*Primary Examiner*—Jane T. Fan
*Attorney, Agent, or Firm*—Roy D. Meredith; Jack L. Tribble

[57] ABSTRACT

Novel aminopyridones inhibit HIV reverse transcriptase, and are useful in the prevention or treatment of infection by HIV and the treatment of AIDS, either as compounds, pharmaceutically acceptable salts, pharmaceutical composition ingredients, whether or not in combination with other antivirals, anti-infectives, immunomodulators, antibiotics or vaccines. Methods of treating AIDS and methods of preventing or treating infection by HIV are also described.

4 Claims, No Drawings

INHIBITORS OF HIV REVERSE TRANSCRIPTASE

This is a continuation of application Ser. No. 07/799,915, filed Nov. 26, 1991 now abandoned which is a continuation of Ser. No. 07/539,681 filed Jun. 18, 1990 now abandoned.

The present invention is concerned with compounds which inhibit the reverse transcriptase encoded by human immunodeficiency virus (HIV) or pharmaceutically acceptable salts thereof and are of value in the prevention of infection by HIV, the treatment of infection by HIV and the treatment of the resulting acquired immune deficiency syndrome (AIDS). It also relates to pharmaceutical compositions containing the compounds and to a method of use of the present compounds and other agents for the treatment of AIDS & viral infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is reverse transcription of the RNA genome by a virally encoded reverse transcriptase to generate DNA copies of HIV sequences, a required step in viral replication. It is known that some compounds are reverse transcriptase inhibitors and are effective agents in the treatment of AIDS and similar diseases, e.g., azidothymidine or AZT.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)].

Applicants demonstrate that the compounds of this invention are inhibitors of HIV reverse transcriptase. The inhibition is very specific, since there is little or no inhibition of the reverse transcriptases of AMV, MMLV or SIV. Further, the compounds of the present invention do not require bio-activation to be effective. They are also generally more potent than AZT.

BRIEF DESCRIPTION OF THE INVENTION

Compounds of formula I, as herein defined, are disclosed. These compounds are useful in the inhibition of HIV reverse transcriptase, the prevention of infection by HIV, the treatment of infection by HIV and in the treatment of AIDS and/or ARC, either as compounds, pharmaceutically acceptable salts (when appropriate), pharmaceutical composition ingredients, whether or not in combination with other antivirals, anti-infectives, immunodoulators, antibiotics or vaccines. Methods of treating AIDS, methods of preventing infection by HIV, and methods of treating infection by HIV are also disclosed.

DETAILED DESCRIPTION OF THE INVENTION AND PREFERRED EMBODIMENTS

This invention is concerned with the use of compounds of formula I, combinations thereof, or pharmaceutically acceptable salts thereof, in the inhibition of HIV reverse transcriptase, the prevention or treatment of infection by HIV and in the treatment of the resulting acquired immune deficiency syndrome (AIDS). Compounds of formula I are defined as follows:

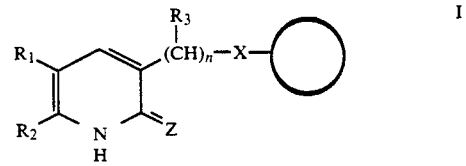

wherein:
X is NH, O or S;
Z is O or S;
n is 1-4;
$R_1$ is
 (i) $C_{1-8}$alkyl, unsubstituted or substituted with one or two of $C_{1-3}$alkoxy, halo, $C_{1-4}$alkylamino, $C_{1-4}$-di-alkylamino, or $C_{1-3}$alkylthio,
 (ii) $C_{1-3}$alkylthio
 (iii) $C_{1-3}$alkoxy; or
 (iv) halo;
$R_2$ is H, methyl or ethyl, unsubstituted or substituted with one or two of methoxy, methylamino, dimethylamino or methylthio
$R_3$ is H or $C_{1-8}$ alkyl;
◯ is aryl or heterocycle, each unsubstituted or substituted with one or more of
 (a) $C_{1-6}$ alkyl,
 (b) $C_{1-6}$ alkoxy unsubstituted or substituted with hydroxy-$C_{1-4}$ alkyl,
 (c) amino,
 (d) $C_{1-6}$ alkyl amino,
 (e) di($C_{1-6}$ alkyl)amino,
 (f) amino-$C_{1-8}$ alkyl,
 (g) $C_{1-8}$ alkyl-amino-$C_{1-8}$ alkyl,
 (h) di-($C_{1-6}$ alkyl)amino $C_{1-8}$ alkyl,
 (i) hydroxyl, or
 (j) halogen,
with the proviso that heterocycle is not phthalimide.

One embodiment of the present invention is Formula I compounds limited as follows:
$R_1$ is $C_{1-4}$ alkyl;
$R_2$ is H or $CH_3$;
aryl is
 (a) naphthyl, unsubstituted or substituted with one or more of $C_{1-6}$ alkyl, halogen or hydroxyl;
 (b) phenyl, unsubstituted or substituted with one or more of $C_{1-6}$ alkyl, halogen or hydroxyl; or
 (c) biphenyl.

A second embodiment are compounds further limited, wherein aryl is 2-naphthyl, 2-naphthyl substituted with methyl, 2-naphthyl substituted with chloro; phenyl; 2-hydroxyphenyl, 2-hydroxyphenyl substituted with methyl, or 2-hydroxyphenyl substituted with chloro.

A third embodiment encompasses compounds further limited, wherein aryl is 2-naphthyl, phenyl or 2-hydroxyphenyl.

A fourth embodiment encompasses compounds of Formula I wherein Heterocycle is thienyl, oxazolyl, thiazolyl, triazolyl, pyridyl, pyrazinyl, benzothienyl, quinolinyl, isoquinolinyl, benzimidazolyl, benzofuranyl, benzothiazolyl, benzoxazolyl unsubstituted or substituted with one or more of $C_{1-6}$ alkyl or halogen or hydroxyl, naphth [3,2-d] oxazolyl, oxazolo [4,5-b] pyridyl, chromone, or benzopyrimidinone.

A fifth embodiment covers compounds having heterocycle further limited to 2-oxazolyl, 2-pyridyl, 2-benzothienyl, 2-quinolinyl, 2-benzimidazolyl, 2-benzofuranyl, 2-benzothiazolyl, 2-benzoxazolyl, methyl substituted 2-benzoxazolyl, halo substituted 2-benzoxazolyl, hydroxyl substituted 2-benzoxazolyl, or 2-oxazolo [4,5-b] pyridyl.

A sixth embodiment covers compounds having heterocycle further limited to 2-benzoxazolyl, 7-methyl-2-benzoxazolyl, 4,7-dimethyl-2-benzoxazolyl, 7-chloro-2-benzoxazolyl, or 4,7-dichloro-2-benzoxazolyl.

The compounds of the present invention, may have asymmetric centers and occur as racemates, racemic mixtures and as individual diastereomers, with all isomeric forms being included in the present invention.

When any variable (e.g., aryl, heterocycle, $R_1$, $R_2$, $R_3$, etc.) occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein, means fluoro, chloro, bromo and iodo.

As used herein, with exceptions as noted, "aryl" is intended to mean any stable monocyclic, bicyclic or tricyclic carbon ring of up to 7 members in each ring, wherein at least one ring is aromatic. Examples of such aryl elements include phenyl, naphthyl, tetrahydronaphthyl, biphenyl, phenanthryl, anthryl or acenaphthyl.

The term heterocycle or heterocyclic, as used herein except where noted, represents a stable 5- to 7-membered monocyclic or stable 8- to 11-membered bicyclic or stable 11-15-membered tricyclic heterocyclic ring which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, benzofuranyl, tetrahydropyranyl, thienyl, benzothienyl, thiamorpholinyl, thiamorpholinyl sulfoxide, thiamorpholinyl sulfone, and oxadiazolyl. Heterocycle does not include phthalimide.

In the compounds of formula I, $R_1$, $R_2$ and $R_3$ include but are not limited to the following substituents, listed in tabular form.

TABLE

| $R_1$ | $R_2$ | $R_3$ |
| --- | --- | --- |
| $CH_3$ | H | H |
| $CH_2OCH_3$ | H | H |
| $CH_2NHCH_3$ | H | H |
| $CH_2CH_3$ | H | H |
| $CH_2CH_2Cl$ | H | H |
| $CH_2CH_2NHCH$ | H | H |
| $CH_3$ | $CH_3$ | H |
| $CH_3OCH_3$ | $CH_3$ | H |
| $CH_2NHCH_3$ | $CH_3$ | H |
| $CH_2CH_3$ | $CH_3$ | H |
| $CH_2CH_2Cl$ | $CH_3$ | H |
| $CH_2CH_2NHCH_3$ | $CH_3$ | H |
| Cl | H | H |
| Cl | $CH_3$ | H |
| Cl | $CH_2CH_3$ | H |
| $CH_3$ | $CH_2CH_3$ | H |
| $CH_2OCH_3$ | $CH_2CH_3$ | H |
| $CH_2NHCH_3$ | $CH_2CH_3$ | H |
| $CH_2CH_3$ | $CH_2CH_3$ | H |
| $CH_2CH_2Cl$ | $CH_2CH_3$ | H |
| $CH_2CH_2NHCH_3$ | $CH_2CH_3$ | H |
| $CH_2CH_3$ | $CH_3$ | $CH_3$ |
| $CH_2CH_2Cl$ | $CH_3$ | $CH_2CH_3$ |
| $CH_2CH_2NHCH_3$ | $CH_3$ | $CH_2CH(CH_3)CH_3$ |
| $CH_2CH_3$ | Cl | $CH_3$ |

In the synthesis of the amino pyridones (3) of this invention, the procedures and protocols of U.S. Pat. No. 3,721,676 can be followed for making many intermediates as well as some of the phthalimide products, which patent is incorporated by reference for these purposes. Applicants here provide preferred methods of synthesis, outlined below.

The 3-nitropyridone of the first step in the synthesis of 3 may be formed by a simultaneous condensation and cyclization of

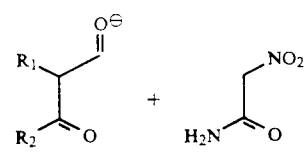

in the presence of a base such as piperidinium acetate. Nitroacetamide is prepared according to Brownstein, S. K., J. Org. Chem. 23, 113 (1958). The 3-nitropyridone products of the first step can also be prepared by direct nitration of 3-unsubstituted pyridones. The 3-nitropyridone product of the first step

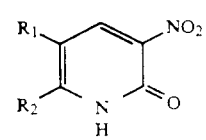

1 is reduced to

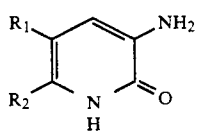

in a second step, preferably catalytic reduction (when sulfur atoms are not present) in the presence of e.g. $H_2$ gas and Pd on carbon catalyst in a solvent such as ethanol. See, e.g., Okafor, C. O. et al., J. Heterocyclic Chem. 20, 199 (1983). Alternatively, the reduction of the second step (including when sulfur atoms are present) can be performed by chemical means, e.g. with NaSH, $Na_2S_2O_4$, Fe+$CaCl_2$, $H_2S$, or Sn+HCl. Reduction with iron in the presence of calcium chlorides is described in Okafor, C. O., J. Org. Chem. 47, 592 (1982). A third step, the final process giving rise to the compounds of this invention,

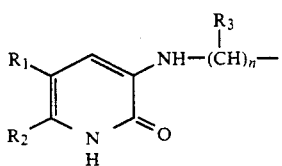

involves a coupling reaction, either by alkylation with an alkylhalide or a reductive alkylation with an aldehyde.

Carba derivatives (9), having alkylene bridges between the pyridone ring and the heterocyclic or aromatic entity attached at the 3-position, may be made by the following methods, the first being the preferred method.

In a first step 3-cyano-2-(1H) pyridinone is prepared by a simultaneous condensation and cyclization of

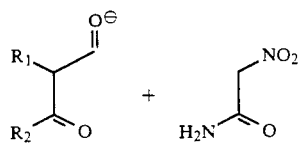

in the presence of base such as piperidinium acetate or pyrrolidine acetate. The resulting 3-cyano-2-(1H) pyridone,

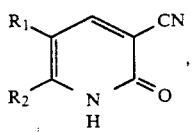

is heated in the presence of phosphorus pentachloride (sometimes in combination with $POCl_3$) to form the corresponding chloro pyridine,

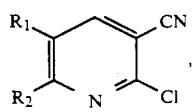

a conventional method of converting pyridones to chloropyridines. $PBr_3$ is useful for making the corresponding bromine derivative of product 5. Product 5 is then subjected to nucleophilic substitution to attach an alkoxy protecting group:

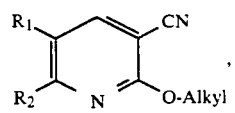

Reduction in the presence of, for example, diisobutyl aluminum hydride, yields

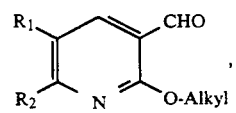

which is a conventional method of reducing nitriles to aldehydes. An alternative reducing agent for the synthesis of 7 is lithium trialkoxy aluminum hydride.

Condensation in the presence of base at very low temperature (preferably at least $-100°$ C.) with an alkyl-substituted aryl or alkyl substituted heterocycle yields

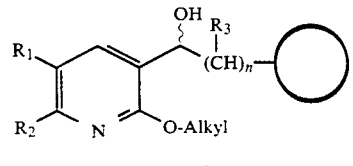

(N = 1)

(The Witting approach, infra, is preferable when n is more than 1.) Dehydration of the alcohol, and dealkylation followed by hydrogenation results in the compounds of the invention, wherein $X=CH_2$,

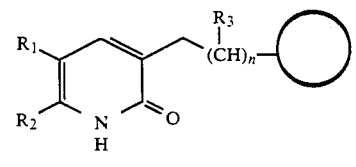

(n = 1)

The dealkylation is typically carried out with pyridine hydrochloride in the presence of heat. The dehydration need not occur in the same reaction, but may be performed separately by conventional means. The standard catalyst for hydrogenation to produce product 9 is palladium, but other noble metals may substitute. Alternatively, the hydrogenation can be carried out with diimide or Raney nickel. $BCl_3$ or $BBr_3$ at low temperature is useful for performing dealkylation without dehydration.

A second alternative variation on the final 3 steps is the Wittig approach, wherein the aldehyde derivative (product 7 above) is reacted with aryl or heterocycle, each substituted with alkylene triphenylphosphorane. The resulting condensation yields an unsaturated alkylene bridge, which is then hydrogenated to yield product 9 compounds above. The advantage of the Wittig approach is that it is preferable for synthesis of compounds of formula 9 wherein n is 2 or more, i.e. with longer alkylene bridges. Also, the Wittig approach is preferable for compounds of Formula I having labile substituents on the heterocycle, particularly halogens.

A third, more lengthy method of making carba derivatives is illustrated in example 4. Briefly, nitrile (4) is hydrolyzed with acid to the corresponding carboxylic acid. Then a three step conversion to an alcohol is performed, followed by oxidation to aldehyde 7. Condensation of the aryl/heterocycle ring is then carried out with the resulting aldehyde as described above.

The transposed connecting chain amino derivatives (12) of the present invention are prepared from product 6 above. Hydrogenation with, e.g., palladium on carbon, yields

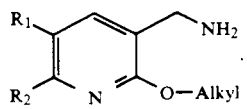

Other ways of hydrogenation of product 6 include reduction with LiAlH$_4$. Subsequent nucleophilic substitution with an appropriately activated halogenated aryl or an appropriately activated halogenated heterocycle produces the secondary amine,

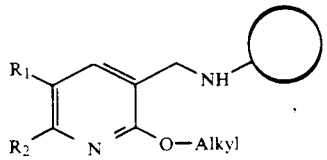

which is dealkylated with, for example, pyridine•HCl and heat, to produce the compounds of this invention:

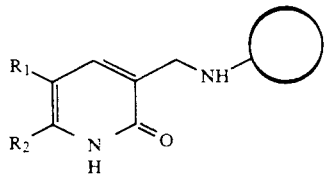

This is specifically illustrated by Example 10.

Alternatively, the transposed connecting chain amino derivatives (12) are prepared from product 7 above, by a reductive amination sequence with amino-substituted aryl or amino-substituted heterocycle. The initial acid-catalyzed condensation product is reduced with, e.g., NaBH$_4$ or NaCNBH$_3$, to yield

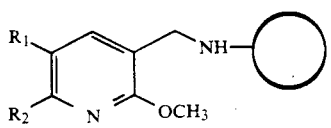

Dealkylation yields the amino compounds of the present invention, wherein X is NH:

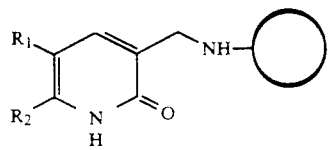

Typically, this final step is carried out with pyridine•HCl in the presence of heat. See also Example 12 for illustration.

2-Thio derivatives (15) are typically prepared by thiolating product 5 above with appropriate reagent such as t-butylmercaptan, to yield

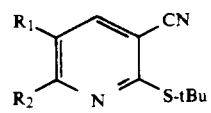

This compound now has a protecting group for the sulfur at the 2-position. The rest of the molecule can be constructed, and, as a final step, dealkylation in pyridine hydrochloride with heat results with

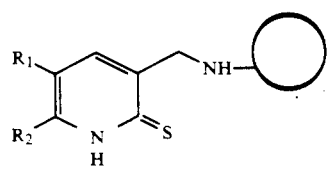

Example 11 illustrates this synthesis. Direct thiolation with Lawesson's Reagent is also useful for preparing 2-thio derivatives, as provided in specific detail in Example 13.

A procedure avails ether linkages at the 3-position of the pyridone ring (18), as provided by way of illustration in Example 9. Product 1 above is transformed in three steps into intermediate 16,

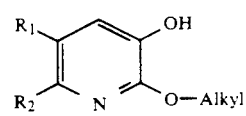

which is subsequently condensed with a halogenated aryl or halogenated heterocycle, in the presence of a base such as sodium hydride to yield

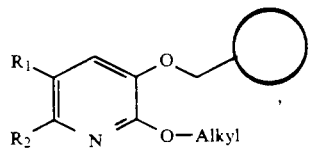

which is dealkylated with pyridine hydrochloride to yield

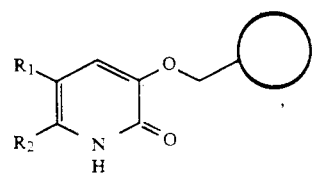

Modification by conventional methodology permits the preparation of the thio analog:

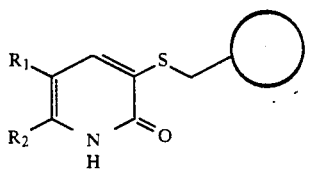

19

Transposed ether linkages at the 3-position of the pyridones (21) in this invention can also be prepared by a simple two step procedure. Intermediate 20

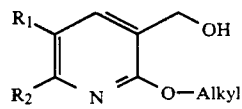

20 is reacted with a halogenated aryl or halogenated heterocycle and a base (NaH in DMF) to yield an alkylated product. Dealkylation is performed with e.g. pyridine•HCl to result in desired product 21:

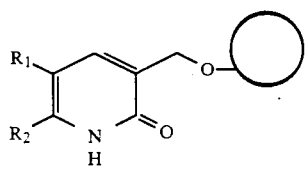

21

Phthalimide derivatives (22) are readily prepared in a one step synthesis. Intermediate 2 is refluxed with N-(hydroxymethyl)-phthalimide (which is commercially available) in ethanol. The resulting condensation product is

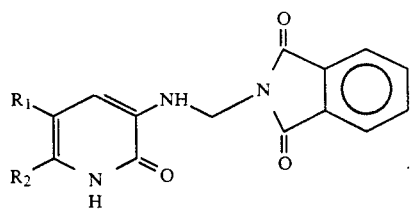

22

Carba derivatives, transposed linkages and 2-thiolated varieties are synthesized by conventional and known techniques analogous to those provided herein:

The compounds of the present inventions are useful in the inhibition of HIV reverse transcriptase, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, accidental needle stick, or exposure to patient blood during surgery.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

The compounds of this invention can be administered orally to humans in a dosage range of 1 to 100 mg/kg body weight in divided doses. A preferred dosage range is 1 to 10 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV reverse transcriptase inhibitor compounds with one or more agents useful in the treatment of AIDS. For example, the compounds of this invention may be effectively administered, whether at periods of pre-exposure and/or post-exposure, in combination with effective amounts of the AIDS antivirals, immunomodulators, anti-infectives, or vaccines of Table I.

TABLE I

| Drug Name | Manufacturer | Indication |
|---|---|---|
| ANTIVIRALS | | |
| AL-721 | Ethigen (Los Angeles, CA) | ARC, PGL HIV positive, AIDS |
| Recombinant Human Interferon Beta | Triton Biosciences (Almeda, CA) | AIDS, Kaposi's sarcoma, ARC |
| Acemannan | Carrington Labs (Irving, TX) | ARC (See also immunomodulators) |
| Cytovene Ganciclovir | Syntex (Palo Alto, CA) | sight threatening CMV peripheral CMV retinitis |
| d4T Didehydrodeoxythymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immunomodulators) |
| Foscarnet Trisodium Phosphonoformate | Astra Pharm. Products, Inc. (Westborough, MA) | CMV retinitis, HIV infection, other CMV infections |
| Dideoxycytidine; ddC | Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Retrovir Zidovudine; AZT | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination w/other therapies, post-exposure prophylaxis in health care workers |
| Rifabutin Ansamycin LM 427 | Adria Laboratories (Dublin, OH) Erbamont (Stamford, CT) | ARC |
| Dextran Sulfate | Ueno Fine Chem. Ind. Ltd. (Osaka, Japan) | AIDS, ARC, HIV positive asymptomatic |
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| IMMUNO-MODULATORS | | |
| Antibody which neutralizes pH labile alpha aberrant Interferon in an immuno adsorption column | Advanced Biotherapy Concepts (Rockville, MD) | AIDS, ARC |
| AS-101 | Wyeth-Ayerst Labs. (Philadelphia, PA) | AIDS |
| Bropirimine | Upjohn (Kalamazoo, MI) | advanced AIDS |
| Acemannan | Carrington Labs, Inc. (Irving, TX) | AIDS, ARC (See also antivirals) |
| CL246,738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also anti- |

TABLE I-continued

| Drug Name | Manufacturer | Indication |
|---|---|---|
| Gamma Interferon | Genentech (S. San Francisco, CA) | virals) ARC, in combination w/TNF (tumor necrosis factor) |
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoeschst-Roussel (Somerville, NJ) Immunex (Seattle, WA) | AIDS |
| Granulocyte Macrophage Colony Stimulating Factor | Schering-Plough (Madison, NJ) | AIDS |
| HIV Core Particle Immunostimulant | Rorer (Ft. Washington, PA) | AIDS, in combination w/Retrovir seropositive HIV |
| IL-2 Interleukin-2 | Cetus (Emerycille, CA) | AIDS, in combination w/Retrovir |
| IL-2 Interleukin-2 | Hoffman-La Roche (Nutley, NJ) | AIDS, ARC, HIV, in combination w/Retrovir |
| Immune Globulin Intravenous (human) | Cutter Biological (Berkeley, CA) | pediatric AIDS, in combination w/Retrovir |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute (Miami, FL) | AIDS, ARC |
| INTRON A Alpha-2 Interferon | Schering Plough (Madison, NJ) | Kaposi's sarcoma w/Retrovir: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposi's sarcoma |
| Granulocyte Colony Stimulating Factor | Amgen (Thousand Oaks, CA) | AIDS, in combination w/Retrovir |
| rCD4 Recombinant Soluble Human CD4 | Genentech (S. San Francisco, CA) | AIDS, ARC |
| rCD4-IgG hybrids | | AIDS, ARC |
| Recombinant Soluble Human CD4 | Biogen (Cambridge, MA) | AIDS, ARC |
| Roferon-A Interferon Alfa 2a | Hoffman-La Roche (Nutley, NJ) | Kaposi's sarcoma AIDS, ARC, in combination w/Retrovir |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with Primaquine | Upjohn (Kalamazoo, MI) | PCP |
| Diflucan Fluconazole | Pfizer (New York, NY) | cryptococcal meningitis, candidiasis |
| Pastille Nystatin Pastille | Squibb Corp. (Princeton, NJ) | prevention of oral candidiasis |
| Ornidyl Eflornithine | Merrell Dow (Cincinnati, OH) | PCP |
| Pentamidine Isethionate (IM & IV) | LyphoMed (Rosemont, IL) | PCP treatment |
| Piritrexim | Burroughs Wellcome (Rsch. Triangle Park, NC) | PCP treatment |
| Pentamidine | Fisons Corporation | PCP prophylaxis |

TABLE I-continued

| Drug Name | Manufacturer | Indication |
|---|---|---|
| isethionate for inhalation | (Bedford, MA) | |
| Spiramycin | Phone-Poulenc Pharmaceuticals (Princeton, NJ) | cryptosporidial diarrhea |
| Intraconazole-R51211 | Janssen Pharm. (Piscataway, NJ) | histoplasmosis; cryptococcal meningitis |
| Trimetrexate | Warner-Lambert | PCP |
| OTHER | | |
| Recombinant Human Erythropoietin | Ortho Pharm. Corp. (Raritan, NJ) | severe anemia assoc. and Retrovir therapy |
| Megestrol Acetate | Bristol-Myers (New York, NY) | treatment of anorexia assoc. w/AIDS |
| Total Enteral | Norwich Eaton Pharmaceuticals (Norwich, NY) | diarrhea and malabsorption related |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

EXAMPLE 1

Preparation of 5-ethyl-6-methyl-3-(2-napthylmethylamino)-2-(1H)-pyridinone

Step A) Preparation of 5-ethyl-6-methyl-3-nitro-2-(1H)-pyridinone

A mixture of 2-ethyl-3-oxobutanal, sodium salt (7.5 g, 55 mmol), nitroacetamide (6.6 g, 63 mmol), aqueous piperidinium acetate (4.4 mL) [prepared from glacial acetic acid (42 mL), water (100 mL) and piperidine (72 mL)] in water (45 mL) was stirred at room temperature for 22 hours. The yellow precipitate was collected by filtration and air dried to yield 8.0 g (80%) of 5-ethyl-6-methyl-3-nitro-2-(1H)-pyridinone.

Step B) Preparation of 3-amino-5-ethyl-6-methyl-2-(1H)-pyridinone

A yellow solution of the 5-ethyl-6-methyl-3-nitro-2-(1H)-pyidinone (10 g, 55 mmol) in a mixture of methanol and tetrahydrofuran (100 mL, 1:1 v/v) was reduced catalytically in the presence of 7% palladium on charcoal (0.7 g) under an atmosphere of hydrogen (50 psi) at room temperature over a period of 3.5 hours. The resultant mixture was filtered through a small pad of Celite. The filtrate was concentrated under reduced pressure (15 torr) to provide 5.7 g (68%) of the corresponding aminopyridone.

Step C) Preparation of 5-ethyl-6-methyl-3-(2-napthylmethylamino)-2-(1H)-pyridinone A mixture of 3-amino-5-ethyl-6-methyl-2-(1H)-pyridinone (3.0 g, 20 mmol), 2-bromomethylnapthalene (4.4 g, 20 mmol), triethylamine (2.0 g, 20 mmol) in acetonitrile (200 mL) was heated under reflux for 4 hours. The resultant mixture was allowed to cool to room temperature and concentrated under reduced pressure (15 torr). The residue was then subjected to column chromatography on silica gel (300 g, elution with methanol-chloroform, 5:95 v/v). Collection and concentration of appropriate fractions provided 2.4 g (42%) of the napthylmethylaminopyridone.

Anal. Calcd for $C_{19}H_{20}N_2O$: C, 75.71; H, 7.02; N, 9.30. Found: C, 75.73; H, 6.71; N, 9.13.

EXAMPLE 2

3-[(2-Benzoxazolymethyl)amino]-5-ethyl-6-methyl-2-(1H)-pyridinone

A solution of 3-amino-5-ethyl-6-methyl-2-(1H)-pyridinone (152 mg, 1.0 mmol), 2-chloromethyl-1,3-benzoxazole (1.07 mmol) and triethylamine (0.14 mL, 1.0 mmol) in acetonitrile (10 mmL) was stirred at reflux for 24 hrs. After concentrating under reduced pressure, the residue was flash chromatographed over silica gel. Elution with 5% MeOH- 95% CHCl$_3$ gave 132 mg of product which was recrystallized from EtOH-water to give 95 mg of analytically pure product, mp 202°-203° C., with initial melting at 179° followed by resolidification. Anal. Calcd for $C_{16}H_{17}N_3O_2$: C, 67.83, H, 6.05; N, 14.83 Found: C, 67.71; H, 6.03; N, 14.76.

EXAMPLE 3

3-[(2-Benzothiazolylmethyl)amino]-5-ethyl-6-methyl-2-(1H)-pyridinone

A solution of 3-amino-5-ethyl-6-methyl-2-(1H)-pyridinone (152 mg, 1.0 mmol), 2-chloromethyl-1,3-benzthiazole (184 mg, 1.0 mmol) and triethylamine (0.14 mL, 1.0 mmol) in absolute ethanol (5 mL) was stirred at reflux for 24 hours. After filtering and concentrating under reduced pressure, the residue was flash chromatographed over silica gel. Elution with 4% MeOH-96% CHCl$_3$ gave 233 mg of product. Recrystallization from EtOH-water gave 77 mg of analytically pure product, mp 209°-210° C. Anal. Calcd for $C_{16}H_{17}N_3OS$: C, 67.83; H, 6.05; N, 14.83. Found: C, 67.71; H, 6.03; N, 14.70.

EXAMPLE 4

3-[2-(Benzoxazol-2-yl)ethyl]-5-ethyl-6-methyl-2-(1H)-pyridinone

Step A: Preparation of 3-cyano-5-ethyl-6-methyl-2-(1H)-pyridinone

According to the method described in J.Heterocyclic Chem., 24, 351 (1987), a mixture of 2-ethyl-3-oxobutanal, sodium salt (37.5 g, 0.275 mmol), cyanoacetamide (25.2 g, 0.30 mol), aqueous piperidinium acetate (22 mL) [prepared from glacial acetic acid (4.2 mL), water (10 mL) and piperidine (7.2 mL)] in water (775 ml) was refluxed for four hours. Glacial acetic acid (30 ml) was added cautiously (much foaming) as the product precipitated. Upon cooling to room temperature, the product was collected by filtration, washed with cold water and air dried to yield 22.3 g (50%), m.p. 237°–240° C.

Step B: Preparation of 5-ethyl-6-methyl-2-(1H)-pyridinone-3-carboxylic acid

An initial suspension of 5-ethyl-6-methyl-2-(1H)-pyridinone (4.86 g, 30 mmol) in 6N HCl (100 mL) was heated at reflux for twenty hours. Upon cooling, the product crystallized and was collected by filtration, washed with cold water and air dried to yield 3.73 g (69%).

Step C: Preparation of methyl 2-chloro-5-ethyl-6-methyl nicotinate

A mixture of 5-ethyl-6-methyl-2-(1H)-pyridinone-3-carboxylic acid (3.62 g, 20 mmol) and phosphorus pentachloride (4.38 g, 21 mmol) was heated, under a nitrogen atmosphere, at 100°–120° C. for 1.5 hours. The cooled residue was diluted with chloroform (70 mL) and then methanol (15 mL) was added. After stirring for 2–16 hours, the solution was poured into ice/water. The organic layer was separated and washed successively with water, saturated aqueous $NaHCO_3$, dried ($Na_2SO_4$), filtered and the solvent evaporated. This dark amber oil was dissolved in hexane, filtered through a pad of charcoal and the solvent evaporated to yield 3.31 g (78%) of pure product as a light yellow oil.

Step D: Preparation of methyl 2-methoxy-5-ethyl-6-methylnicotinate

To a solution of sodium metal (0.55 g, 24 mmol) dissolved in anhydrous methanol (15 mL), under a nitrogen atmosphere, was added a solution of methyl 2-chloro-5-ethyl-6-methylnicotinate (3.18 g, 14.9 mmol) in dry methanol (5 mL). This solution was refluxed and monitored by tlc (thin layer chromatogram) until the starting material had been consumed (about 24 hours). The cooled mixture was diluted with diethyl ether (50 mL), washed with water, saturated aqueous $NaHCO_3$, dried ($Na_2SO_4$), filtered and the solvent evaporated to yield 2.28 g (73) of pure product as a light yellow oil.

Step E: Preparation of 2-methoxy-3-hydroxymethyl-5-ethyl-6-methyl pyridine

To a solution of methyl 2-methoxy-5-ethyl-6-methylnicotinate (2.28 g, 10.9 mmol) in anhydrous tetrahydrofuran (50 mL), under a nitrogen atmosphere, was added cautiously lithium aluminum hydride (0.77 g, 20 mmol). After refluxing this mixture for 15–20 hours, saturated aqueous $Na_2SO_4$ was added carefully to quench the cooled reaction mixture. This mixture was diluted with more THF, dried ($Na_2SO_4$), filtered and the solvent evaporated. This residue was chased with ethanol/toluene to remove traces of water and triturated with hexane as the product slowly crystallized out to give 1.30 g (66%), mp 53°–55° C.

Step F: Preparation of 2-methoxy-5-ethyl-6-methyl nicotinaldehyde

Activated manganese dioxide (2.0 g) was added to a solution of 2-methoxy-3-hydroxymethyl-5-ethyl-6-methylpyridine (1.18 g, 6.5 mmol) in dry benzene (20 mL) and refluxed 5–10 hours. The warm suspension was filtered through a pad of anhydrous $Na_2SO_4$ and evaporated to yield 1.05 g (90%) of a viscous oil which solidified.

Step G: Preparation of 2-[2(R/S)-hydroxy-2-(2-methoxy-5-ethyl-6-methyl-pyridin-3-yl)ethyl]-benzoxazole To a solution of 2-methylbenzoxazole (226 mg, 1.7 mmol) in anhydrous THF (4 mL), cooled to −100° C. under an argon atmosphere, was added 1.6M n-butyllithium/hexane (1.05 mL) slowly over 35 minutes. After 0.5 hour a solution of 2-methoxy-5-ethyl-6-methyl-nicotinaldehyde (300 mg, 1.7 mmol) in dry THF (1 mL) was added dropwise. The reaction was allowed to warm to room temperature and poured onto crushed ice. This mixture was extracted with diethyl ether. The combined extracts were dried ($MgSO_4$) and the solvent removed to give an oil which was flash chromatographed over silica gel. Elution with ethyl acetate/hexane (1:19) gave 340 mg (65%) of analytically pure racemic product, mp 102°–103° C.

Anal. Calcd for $C_{18}H_{20}N_2O_3.0.1\ H_2O$: C, 68.81; H, 6.48; N, 8.92. Found: C, 68.80; H, 6.76; N, 8.95.

Step H: Preparation of 3-[2-(benzoxazol-2-yl)-ethenyl]-5-ethyl-6-methyl-2-(1H)-pyridinone A mixture of 2-[2(R/S)-hydroxy-2-(2-methoxy-5-ethyl-6-methylpyridin-3-yl)ethyl]benzoxazole (72 mg, 0.23 mmol) and pyridine hydrochloride (133 mg, 1.2 mmol), under a nitrogen atmosphere, was placed in a preheated oil bath (165° C.) for 5 minutes. The reaction flask was removed, cooled, and water added to give a solid. This crude product was extracted into chloroform, dried ($MgSO_4$) and the solvent evaporated to yield 49 mg (75%) of pure product. Recrystallization from methanol gave 15 mg of analytically pure product, mp 262°–264° C. Anal. Calcd for $C_{17}H_{16}N_2O_2$: C, 72.83; H, 5.75; N, 10.00. Found: C, 72.93; H, 5.95; N, 9.99.

Step I: Preparation of 3-[2-(benzoxazol-2-yl)ethyl]-5-ethyl-6-methyl-2-(1H)-pyridinone A solution of 80% pure 3-[2-(benzoxazol-2-yl)ethenyl]-5-ethyl-6-methyl-2-(1H)-pyridinone (200 mg) in methanol/ethanol/THF (25 mL, 1:1:1) was hydrogenated at atmospheric pressure over 5% palladium/charcoal for four hours. After filtering off the catalyst, the solvents were evaporated and the residue flash chromatographed over silica gel. Elution with 2% methanol-98% chloroform gave 75 mg of analytically pure product, mp 155°–156.5° C.

Anal. Calcd. for $C_{17}H_{18}N_2O_2$ C, 72.31; H, 6.43; N, 9.92. Found: C, 72.45; H, 6.52; N, 9.99.

EXAMPLE 5

Another, simpler procedure for the synthesis of the product of Example 4 is as follows.

Step A: Preparation of 3-cyano-5-ethyl-6-methyl-2-(1H)-pyridinone

Accordingly to the method described in J. Heterocyclic Chem., 24, 351 (1987), a mixture 2-ethyl-3-oxobutanol, sodium salt (37.5 g, 0.275 mol), cyanoacetamide (25.2 g, 0.30 mol), aqueous piperidinium acetate (22 mL) [prepared from glacial acetic acid (4.2 mL), water (10 mL) and piperidine (7.2 mL)] in water (775 ml) was refluxed for four hours. Glacial acetic acid (30 ml) was added cautiously (much foaming) as the product precipitated. Upon cooling to room temperature, the product was collected by filtration, washed with cold water and air dried to yield 22.3 g (50%), m.p. 237°–240° C.

New

Step B: Preparation of 2-chloro-3-cyano-5-ethyl-6-methylpyridine

3-Cyano-5-ethyl-6-methyl-2-(1H)-pyridinone (22.9 g, 0.141 mol) and phosphorus pentachloride (33.1 g, 0.159 mol) were intimately mixed and heated at 110°–120° C. for one hour. The liquified solids were poured onto crushed ice and water and the semi-solid was extracted into chloroform. This extract was washed with water, saturated aqueous NaHCO$_3$, dried (Na$_2$SO$_4$), filtered and evaporated. This amber oil was dissolved in hexane and the insoluble material was removed when filtered through a pad of charcoal. Removal of the solvent gave a light yellow oil which solidified (17.7 g). Trituration of this solid with cold hexane yielded 15.6 g (61%) of pure product, m.p. 63°–64° C.

New

Step C: Preparation of 2-methoxy-3-cyano-5-ethyl-6-methylpyridine

Sodium metal (3.25 g, 0.141 mol) was dissolved in dry methanol (100 mL) under a nitrogen atmosphere. When solution was complete, a slurry of 2-chloro-5-ethyl-6-methylpyridine (17.95 g, 99.4 mmol) in dry methanol (70 mL) was added and the reaction was warmed at 60° C. for 15–20 hours. After cooling the reaction mixture, diethyl ether (250 mL) and water (200 mL) were added. The ether layer was separated and washed with water, dried (Na$_2$SO$_4$), filtered and evaporated to give a light yellow solid (17.5 g). This solid was triturated with cold hexane to yield 14.4 g (82%) of pure product, m.p. 59°–61° C.

New

Step D: Preparation of 2-methoxy-5-ethyl-6-methylnicotinaldehyde

To a solution of 2-methoxy-3-cyano-5-ethyl-6-methylpyridine (1.0 g, 5.68 mmol) in dry tetrahydrofuran (50 mL) under a nitrogen atmosphere and cooled to −70° C., was added 1.3M diisobutyl aluminum hydride/THF (17.4 mL, 22.7 mmol). The resulting mixture was allowed to warm to room temperature and stir for 15–20 hours. The reaction mixture was acidified with 1N hydrochloric acid and then neutralized with aqueous sodium bicarbonate. Water was then added and the product extracted into diethyl ether. The etheral extract was dried (Na$_2$SO$_4$), filtered and the solvent evaporated. This residue was flash chromatographed on silica gel eluting with 10% diethyl ether/pentane to give 610 mg (61%) of product.

Step E (old step G): Preparation of 2-[2(R/S)-hydroxy-2-(2-methoxy-5-ethyl-6-methylpyridin-3-yl)ethyl]-benzoxazole To a solution of 2-methylbenzoxazole (226 mg, 1.7 mmol) in anhydrous THF (4 mL), cooled to −100° C. under an argon atmosphere, was added 1.6M n-butyllithium/hexane (1.05 mL) slowly over 35 minutes. After 0.5 hour a solution of 2-methoxy-5-ethyl-6-methylnicotinaldehyde (300 mg, 1.7 mmol) in dry THF (1 mL) was added dropwise. The reaction was allowed to warm to room temperature and poured onto crushed ice. This mixture was extracted with diethyl ether. The combined extracts were dried (MgSO$_4$) and the solvent removed to give an oil which was flash chromatographed over silica gel. Elution with ethyl acetate/hexane (1:19) gave 340 mg (65%) of analytically pure racemic product, mp 102°–103° C.

Anal. Calcd for C$_{18}$H$_{20}$N$_2$O$_3$.0.1 H$_2$O: C, 68.81; H, 6.48; N, 8.92. Found: C, 68.80; H, 6.76; N, 8.95.

Step F (old step H): Preparation of 3-[2-(benzoxazol-2-yl)-ethenyl]-5-ethyl-6-methyl-2-(1H)-pyridinone A mixture of 2-[2(R/S)-hydroxy-2-(2-methoxy-5-ethyl-6-methylpyridin-3-yl)ethyl]benzoxazole (72 mg, 0.23 mmol) and pyridine hydrochloride (133 mg, 1.2 mmol), under a nitrogen atmosphere, was placed in a preheated oil bath (165° C.) for 5 minutes. The reaction flask was removed, cooled, and water added to give a solid. This crude product was extracted into chloroform, dried (MgSO$_4$) and the solvent evaporated to yield 49 mg (75%) of pure product. Recrystallization from methanol gave 15 mg of analytically pure product, mp 262°–264° C. Anal. Calcd. for C$_{17}$H$_{16}$N$_2$O$_2$: C, 72.83; H, 5.75; N, 10.00. Found: C, 72.93; H, 5.95; N, 9.99.

Step G (old step I): Preparation of 3-[2-(benzoxazol-2-yl)ethyl]-5-ethyl-6-methyl-2-(1H)-pyridinone A solution of 80% pure 3-[2-(benzoxazol-2-yl)ethenyl]-5-ethyl-6-methyl-2-(1H)-pyridinone (200 mg) in methanol/ethanol/THF (25 mL, 1:1:1) was hydrogenated at atmospheric pressure over 5% palladium/charcoal for four hours. After filtering off the catalyst, the solvents were evaporated and the residue flash chromatographed over silica gel. Elution with 2% methanol-98% chloroform gave 75 mg of analytically pure product, mp 155°–156.5° C.

Anal. Calcd. for C$_{17}$H$_{18}$N$_2$O$_2$ C, 72.31; H, 6.43; N, 9.92. Found: C, 72.45; H, 6.52; N, 9.99.

EXAMPLE 6

3-[2-(4,7-Dimethylbenzoxazol-2-yl)ethyl]-5-ethyl-6-methyl-2-(1H)-pyridinone

Step A: Preparation of 2-methoxy-3-[2-(4,7-dimethylbenzoxazol-2-yl)ethenyl]-5-ethyl-6-methyl-2-pyridine Sodium hydride (60% in mineral oil, 47 mg, 1.15 mmol) was added to a suspension of [(4,7-dimethylbenzoxal-2-yl)methyl]triphenylphosphonium chloride (485 mg, 1.06 mmol) [prepared by heating 2-chloromethyl-4,7-dimethylbenzoxazole with an equimolar amount of triphenylphosphine in refluxing toluene for 15–25 hours] in dry tetrahydrofuran (8 mL) under a nitrogen atmosphere at 25° C. After 15 minutes, solid 2-methoxy-5-ethyl-6-methyl nictotinaldehyde (197 mg, 1.15 mmol) was added to the yellow suspension. This reaction mixture was heated at reflux for 15–25 hours. Upon cooling, this reaction was diluted with chloroform, washed with water, dried (Na$_2$SO$_4$), filtered and the solvent evaporated. This residue was flash chromatographed on silica gel and the product eluted with chloroform to yield 178 mg (55%) of a cis/trans mixture of product as an oil.

Step B: Preparation of 2-methoxy-3-[2-(4,7-dimethylbenzoxazol-2-yl)ethyl]-5-ethyl-6-methylpyridine A solution of crude cis/trans 2-methoxy-3-[4,7-dimethylbenzoxazol-2-yl)ethenyl]-5-ethyl-6-methylpyridine (178 mg, 0.55 mmol) in methanol (4 mL) and tetrahydrofuran (5 mL) containing 5% palladium on charcoal (67 mg) was hydrogenated at atmospheric pressure for 5–15 hours. The catalyst was filtered off and the solution evaporated to yield 161 mg (89%) of product as an oil.

Step C: Preparation of 3-[2-(4,7-dimethylbenzoxazol-2-yl)ethyl]-5-ethyl-6-methyl-2(1H)-pyridinone A mixture of crude 2-methoxy-3-[2-(4,7-dimethylbenzoxazol-2-yl)ethyl]-5-ethyl-6-methylpyridine (161 mg, 0.49 mmol) and pyridine hydrochloride (574 mg, 4.97 mmol) was warmed in a pre-heated oil bath at 140° C. for 15 minutes. The cooled residue was diluted with water and the product extracted into chloroform. This extract was dried (Na$_2$SO$_4$), filtered and the solvent evaporated. This residue was chromatographed on silica gel and eluted with a 0.5 to 2.5% methanol/chloroform gradient to yield 65 mg of pure product. The product was crystallized from diethyl ether to give 38 mg, m.p. 151.5°–153° C.

Anal. Calcd. for C$_{19}$H$_{22}$N$_2$O$_2$•0.15 H$_2$O: C, 72.88; H, 7.18; N, 8.95. Found: C, 72.89; H, 7.16; N, 8.87.

EXAMPLE 7

Preparation of
3-[((4,7-Dimethylbenzoxazol-2-yl)-methyl)amino]-5-ethyl-6-methyl-2(1H)-pyridinone Step A) Preparation of 2-chloromethyl-4,7-dimethylbenzoxazole To a solution of 2,5-dimethyl-6-aminophenol (0.67 g, 4.9 mmol) in methylene chloride, solid ethyl 2-chloroiminoacetate hydrochloride (0.85 g, 4.9 mmol) was added. The resultant slurry was stirred at room temperature for 18 hours, then filtered through a plug of diatomaceous earth and concentrated under reduced pressure (15 torr). The solid residue was subjected to column chromatography on silica gel (50 g, eluted with 1% methanol in chloroform). Collection and concentration of appropriate fractions yielded 0.85 g (89%) of the benzoxazole.

Step B: Preparation of 3-[((4,7-dimethylbenzoxazol-2-yl)methyl)amino]-5-ethyl-6-methyl-2-(1H)-pyridinone A mixture of 3-amino-5-ethyl-6-methyl-2-(1H)-pyridinone (0.23 g, 1.5 mmol), 2-chloromethyl-4,7-dimethylbenzoxazole (0.29 g, 1.5 mmol), diisopropylethylamine (0.39 g, 3 mmol) in acetonitrile (50 mL) was refluxed under an atmosphere of nitrogen for 12 hours. The resultant mixture was concentrated under reduced pressure (15 torr). The residue was then subjected to column chromatography on silica gel (100 g, elution with 4% methanol in chloroform). Collection and concentration of appropriate fractions provided 0.2 g (44%) of the benzoxazolylmethylaminopyridone. Anal. Calcd. for $C_{18}H_{21}N_3O_2$: C, 69.43; H, 6.80; N, 13.49. Found: C, 69.32; H, 6.66; N, 13.47.

EXAMPLE 8

Preparation of
5-ethyl-6-methyl-3-(2-napthylmethylamino)-2-(1H)-pyridinthione

Step A: Preparation of 2-chloro-5-ethyl-6-methyl-3-nitropyridine

A mixture of 5-ethyl-6-methyl-3-nitro-2-(1H)-pyridinone (2.38 g, 13 mmol) and phosphorus pentachloride (3.3 g, 15.6 mmol) was heated under an atmosphere of nitrogen at 140°-150° C. for 15 minutes. The resultant brown oil was then treated with water and the product extracted into chloroform. The organic extract was washed three times with brine, dried over anhydrous sodium sulfate, filtered and concentrated under reduced pressure (15 torr). The residue was passed through a small plug of silica gel, eluted with 2% methanol in chloroform. Collection and concentration of appropriate fractions yielded 1.5 g (57.5%) of the corresponding chloropyridine as a clear pale brown oil.

Step B: Preparation of 2-tert-butylthio-5-ethyl-6-methyl-3-nitropyridine

To a suspension of sodium hydride (0.23 g, 9.8 mmol) in dimethylformamide (DMF, 20 mL) under an atmosphere of nitrogen, 2-methyl-2-propanethiol (1 mL, 8 mmol) was added. After stirring at room temperature for 15 minutes, a clear solution was obtained. Then a solution of 2-chloro-5-ethyl-6-methyl-3-nitropyridine (1.5 g, 7.5 mmol) in DMF (2 mL) was added, and the reacting mixture turned dark green to black in color. After addition was completed, the mixture was stirred for an additional 15 minutes, and then concentrated under reduced pressure (0.1 torr). The residue was subjected to column chromatography on silica gel, eluted with 60% chloroform in hexane. Collection and concentration of appropriate fractions yielded 0.5 g (26%) of the corresponding 2-tert-butylthiopyridine as a bright yellow solid.

Step C: Preparation of 3-amino-2-tert-butylthio-5-ethyl-6-methylpyridine

To a yellow solution of 2-tert-butylthio-5-ethyl-6-methyl-3-nitropyridine (0.5 g, 2 mmol) in methanol (50 mL) at room temperature, a solution of sodium hydrosulfite ($Na_2S_2O_4$, 2.5 g, 14 mmol) in water (25 mL) was added. The resulting white suspension was stirred for an additional five minutes and concentrated under reduced pressure (15 torr). The residue solid was triturated three times with chloroform, and the extracts were combined, dried over sodium sulfate, and concentrated under reduced pressure (15 torr). The resulting residue was then passed through a small plug of silica gel and eluted with 3% methanol in chloroform. Collection and concentration of appropriate fractions yielded 0.3 g (68%) of the aminopyridine.

Step D: Preparation of 2-tert-butylthio-5-ethyl-6-methyl-3-(2-napthylmethylamino)pyridine A mixture of 3-amino-2-tert-butylthio-5-ethyl-6-methylpyridine (0.15 g, 0.67 mmol), 2-bromomethylnapthalene (0.15 g, 0.67 mmol), diisopropylethylamine (86 mg, 0.67 mmol) in acetonitrile (5 mL) was refluxed under an atmosphere of nitrogen for 16 hours. The resultant mixture was concentrated under reduced pressure (15 (torr). The residue was subjected to column chromatography on silica gel (50, elution with 1% methanol in chloroform). Collection and concentration of appropriate fractions provided 98 mg (40%) of the napthylmethylaminopyridine.

Step E: Preparation of 5-ethyl-6-methyl-3-(2-napthylmethylamino)-2-(1H)-pyridinthione A mixture of 2-tert-butylthio-5-ethyl-6-methyl-3-(2-napthylmethylamino)pyridine (98 mg, 0.27 mmol) and pyridine hydrochloride (0.45 g, 3.8 mmol) was heated under an atmosphere of nitrogen at 140° C. until evolution of gas ceased (about 45 minutes). Water was added and the resultant mixture was extracted three times with chloroform. The organic extracts were combined, dried over anhydrous sodium sulfate, filtered and concentrated under reduced pressure (15 torr). The residue was then subjected to column chromatography on silica gel (eluted with 2% methanol in ethyl acetate). Collection and concentration of appropriate fraction yielded 32 mg (36%) of the pyridinethione. Anal. Calcd for $C_{19}H_{20}N_2S \cdot 0.25$ EtOAc: C, 72.68; H, 6.71; N, 8.48. Found: C, 72.41; H, 6.59; N, 8.86.

EXAMPLE 9

3-[(Benzoxazol-2-yl)methoxy]-5-ethyl-6-methylpyridin-2(1H)-one

Step A: Preparation of 2-chloro-3-nitro-5-ethyl-6-methylpyridine

A mixture of 3-nitro-5-ethyl-6-methylpyridin-2(1H)-one (0.91 g, 5.0 mmol) and phosphorus pentachloride (1.25 g, 6.0 mmol), under a nitrogen atmosphere, was heated at 140° C. for 0.5 hours. The cooled mixture was diluted with chloroform and ice water. The separated chloroform layer was then washed with water, saturated aqueous $NaHCO_3$ and dried ($Na_2SO_4$). After filtering through a pad of charcoal, solvent was evaporated to yield 672 mg (67%) of product.

Step B: Preparation of 2-methoxy-3-nitro-5-ethyl-6-methylpyridine

Sodium metal (100 mg, 4.3 mmol) was dissolved in methanol (5 mL) under a nitrogen atmosphere. A solution of 2-chloro-3-nitro-5-ethyl-6-methylpyridine (677 mg, 3.37 mmol) in methanol (5 mL) was added dropwise. The reaction was warmed at 50° C. for four hours. The reaction was cooled, diluted with diethyl ether, the ether layer washed with water, dried ($Na_2SO_4$), filtered through a pad of charcoal and evaporated to yield 535 mg (80%) of product.

Step C: Preparation of 2-methoxy-3-amino-5-ethyl-6-methylpyridine

A solution of 2-methoxy-3-nitro-5-ethyl-6-methylpyridine (535 mg, 2.72 mmol) in methanol (8 mL) and tetrahydrofuran (8 mL) containing 5% palladium on carbon (83 mg) was hydrogenated at atmospheric pressure for 5 hours. The catalyst was filtered off the solvent evaporated to yield 436 mg (98%) of oily product.

Step D: Preparation of 2-methoxy-3-hydroxy-5-ethyl-6-methylpyridine

A batch of 2-methoxy-3-amino-5-ethyl-6-methylpyridine (171 mg, 1.05 mmol) was dissolved in 5% aqueous sulfuric acid (4 mL), cooled in an ice bath, then a solution of sodium nitrite (78 mg, 1.13 mmol) in water (1 mL) was added dropwise. After 0.5 hour, the resulting mixture was added dropwise to 5% aqueous sulfuric acid (6 mL) warmed at 110° C. The solution was stirred for 0.5 hour, cooled and the product extracted into chloroform, then dried ($Na_2SO_4$), filtered and evaporated to yield 77 mg (43%) of product.

Step E: Preparation of 3-[(benzoxazol-2-yl)methoxy]-2-methoxy-5-ethyl-6-methylpyridine A quantity of 60% sodium hydride in mineral oil (24 mg, 0.6 mmol) was added to a solution of 2-methoxy-3-hydroxy-5-ethyl-6-methylpyridine (77 mg, 0.46 mmol) in dry dimethylformamide (2 mL). After gas evolution ceased, 2-(chloromethyl) benzoxazole (100 mg, 0.6 mmol) was added and the reaction mixture warmed at 60° C. for one hour. The reaction was then cooled, diluted with diethyl ether, the ether extract washed with water, dried ($Na_2SO_4$), filtered and evaporated to give 151 mg of crude mixture. This mixture was flash chromatographed on silica gel, eluting with 0.5% methanol/chloroform. Combined appropriate fractions gave 46 mg (32%) of oily product.

Step F: Preparation of 3-[(benzoxazol-2-yl)methoxy]-5-ethyl-6-methylpyridin-2(1H)-one 3[(Benzoxazol-2-yl)methoxy]-2-methoxy-5-ethyl-6-methylpyridine (140 mg, 0.47 mmol) was dissolved in methylene chloride (5 ml) and cooled in an ice bath under an atmosphere of nitrogen. 1M Boron tribomide (2.3 mL, 2.3 mmol) in hexane was added to this solution and the reaction mixture was allowed to warm to room temperature over a 0.75 hour period. This mixture was re-cooled in an ice bath and saturated aqueous $NaHCO_3$ (5 mL) was added to quench the reaction. The methylene chloride layer was dried ($Na_2SO_4$), filtered and evaporated. The residue was triturated with diethyl ether to give 69 mg of crude product. Recrystallization from methanol yielded 60 mg (45%), m.p. 198°-200° C.

Anal. Calcd for $C_{16}H_{16}N_2O_3$: C, 67.59; H, 5.67; N, 9.86. Found: C, 67.59; H, 5.66; N, 9.83.

EXAMPLE 10

3-{[(Benzoxazol-2-yl)amino]methyl}-5-ethyl-6-methyl-2-(1H)-pyridinone

Step A: Preparation of 2-methoxy-3-(aminomethyl)-5-ethyl-6-methylpyridine

A solution of 2-methoxy-3-cyano-5-ethyl-6-methylpyridine (344 mg, 1.95 mmol) in methanol (8 mL) and 4.9M methanolic HCl (5 mL) containing 5% palladium on carbon (100 mg) was hydrogenated at atmospheric pressure for 10–20 hours. The catalyst was filtered off and the solvent evaporated. This residue was made basic with sodium hydroxide and the product was extracted into methylene chloride, dried ($Na_2SO_4$), filtered and evaporated to give 313 mg (89% yield) of oily product.

Step B: Preparation of 2-methoxy-3-{(benzoxazol-2-yl)amino]methyl}-5-ethyl-6-methylpyridine To a solution of 2-methoxy-3-(aminomethyl)-5-ethyl-6-methylpyridine (98 mg, 0.54 mmol) in methanol (1 mL), under a nitrogen atmosphere was added 2-chlorobenzoxazole (0.07 mL, 0.61 mmol), followed by triethylamine (0.076 mL, 0.55 mmol). After two hours, product began to crystallize out. The mixture was stirred for 12 hours and the product (133 mg, 82%) collected by filtration. This material was dissolved in diethyl ethyl, filtered through a charcoal pad and hexane added to the solution. As the ether was boiled off, product crystallized out to give 96 mg, m.p. 141.5°–142.5° C.

Anal. Calcd. for $C_{17}H_{19}N_3O_2$: C, 68.67; H, 6.44; N, 14.13. Found: C, 68.68; H, 6.36; N, 14.07.

Step C: Preparation of 3-{[(benzoxazol-2-yl)amino]-methyl}-5-ethyl-6-methyl-2-(1H)-pyridinone A mixture of 2-methoxy-3-{[(benzoxazol-2-yl)amino]methyl}-5-ethyl-6-methylpyridine (80 mg, 0.269 mmol) and pyridine hydrochloride (335 mg, 2.9 mmol), under a nitrogen atmosphere, was warmed in an oil bath pre-heated to 150° C. for 5 minutes. This solidified mixture was cooled, diluted with water and the crude precipitated product collected by filtration. This material was dissolved in methylene chloride, filtered through a charcoal pad and then diluted with hexane. As the methylene chloride was boiled off the product crystallized out to give 40 mg (53%), m.p. 211°–213° C.

Anal. Calcd for $C_{16}H_{17}N_3O_2$: C, 67.82; H, 6.05; N, 14.83. Found: C, 68.08; H, 6.03; N, 14.86.

EXAMPLE 11

3-{[(Benzoxazol-2-yl)amino]methyl}-5-ethyl-6-methyl-2-(1H)-pyridinthione

Step A: Preparation of 2-t-butylthio-3-cyano-5-ethylpyridine t-Butylmercaptan (0.40 mL, 3.55 mmol) was added to a suspension of 60% sodium hydride in mineral oil (158 mg, 3.85 mmol) in dry dimethylformamide (5 mL). After 10 minutes, when gas evolution ceased, 2-chloro-3-cyano-5-ethyl-6-methylpyridine (542 mg, 3.0 mmol) was added. After stirring for one hour, water was added and product extracted into diethyl ether. This extract was dried ($Na_2SO_4$), filtered and the solvent removed to give 648 mg (92%) of crystalline product, m.p. 63°–66° C.

Step B: Preparation of 2-t-butylthio-3-(aminomethyl)-5-ethyl-6-methylpyridine

To a suspension of lithium aluminum hydride (54 mg, 1.42 mmol) in diethyl ether (10 mL), under a nitrogen atmosphere, was added dropwise a solution of 2-t-butylthio-3-cyano-5-ethylpyridine (222 mg, 0.95 mmol) in diethyl ether (6 mL). After stirring for 3.5 hours at room temperature, the reaction was quenched with saturated aqueous sodium sulfate and the ether layer dried ($Na_2SO_4$), filtered and evaporated to give 219 mg (96%) of crude oily product.

Step C: Preparation of 2-t-butylthio-3-{(benzoxazol-2-yl)amino]methyl}-5-ethyl-6-methylpyridine To a solution of crude 2-t-butylthio-3-(aminomethyl)-5-ethyl-6-methyl pyridine (219 mg, 0.9 mmol) in methanol (2 mL) was added 2-chlorobenzoxazole (0.14 mL, 1.0 mmol), followed by triethyl amine (0.14 mL, 1.0 mmol). After stirring for 12 hours, the solvent was evaporated and the residue dissolved in diethyl ether, which was washed with water, dried ($Na_2SO_4$), filtered and evaporated. This crude residue was flash chromatographed on silica gel eluting with 12% ethyl acetate/hexane. The appropriate fractions were combined, the solvent evaporated and the residue triturated with hexane to give 114 mg (35%) of pure product, m.p. 141°–143° C. Anal. Calcd. for $C_{30}H_{25}N_3OS$: C, 67.57; H, 7.09; N, 11.82 Found: C, 67.78; H, 7.21; N, 11.77.

Step D: Preparation of 3-{[(benzoxazol-2-yl)amino]-methyl}-5-ethyl-6-methylpyridin-2(1H)thione A mixture of 2-t-butylthio-3-{[(benzoxazol-2-yl)amino]methyl}-5-ethyl-6-methylpyridine (78 mg, 0.22 mmol) and pyridine hydrochloride (325 mg, 2.81 mmol) was warmed in a pre-heated oil bath at 150° C. for 25 minutes. The mixture was cooled, diluted with water and the yellow precipitated product was collected by filtration. This residue was dissolved in methylene chloride, filtered through a pad of charcoal and then hexane was added and the methylene chloride boiled off as the product crystallized out to yield 42 mg (64%), m.p. 238°–240° C. Anal Calcd. for $C_{16}H_{17}N_3OS$: C, 64.18; H, 5.72; N, 14.04. Found: C, 63.86; H, 5.69; N, 13.81.

EXAMPLE 12

3-{[1-naphthylamino]methyl}-5-ethyl-6-methyl-2-(1H)-pyridinone

Step A: Preparation of 2-methoxy-3-{[1-naphthylamino]methyl}-5-ethyl-6-methylpyridine A solution of 2-methoxy-5-ethyl-6-methylnicotinaldehyde (100 mg, 0.6 mmol) and 1-aminonaphthalene (80 mg, 0.6 mmol) in ethanol (1 mL) containing p-toluenesulfonic acid (~5 mg) was warmed at 60° C. for 5–15 hours, then cooled and sodium borohydride (40 mg, 1.0 mmol) added. After 0.5 hour, the reaction mixture was diluted with water, acidified with dilute aqueous hydrochloric acid and product extracted into diethyl ether. The extract was dried ($MgSO_4$), filtered a through pad of charcoal and evaporated to yield 177 mg of greenish oil. Trituration of this residue with methanol gave 40 mg of crystalline product, m.p. 82°–83° C.

Anal. Calcd for $C_{20}H_{22}N_2O$: C, 77.48; H, 7.28; N, 9.04 Found: C, 77.42; H, 7.18; N, 8.94.

Step B: Preparation of 3-{[1-napthylamino]methyl}-5-ethyl-6-methyl-2-(1H)-pyridinone A mixture of 2-methoxy-3-{[1-naphthylamino]-methyl}-5-ethyl-6-methylpyridine (125 mg, 0.41 mmol) and pyridine hydrochloride (500 mg, 4.3 mmol) was warmed at 145°–160° C. for 20 minutes. The reaction mixture was then cooled, water added, and the mixture made acidic with dilute aqueous hydrochloride acid. The product was then extracted into chloroform. Chloroform extracts were concentrated and the residue flash chromatographed on silica gel eluting with 5% methanol/95% chloroform. Appropriate fractions were combined and evaporated. The residue was triturated with diethyl ether to give 18.9 mg (15%) of product, m.p. 165°–167° C.

Anal. Calcd. for $C_{19}H_{20}N_2O$: C, 78.05; H, 6.90; N, 9.58 Found: C, 77.81; H, 7.11; N, 9.22.

EXAMPLE 13

3-[2-(Benzoxazol-2-yl)-ethyl]-5-ethyl-6-methyl pyridin-2(1H)-thione

A mixture of 3-[2-(benzoxazol-2-yl)-ethyl]-5-ethyl-6-methyl pyridin-2(1H)-one (150 mg, 0.53 mmol) and 2,4-bis(4-methoxyphenyl)-1,3-dithia-2,4-diphosphetane-2,4-disulfide (Lawesson's Reagent) (485 mg, 1.2 mmol) in dry toluene (4 mL) was refluxed for 6–10 hours. The solvent was evaporated and the reaction residue was flash chromatographed on silica gel eluting with 0.5% methanol/chloroform. The appropriate fractions were combined and crystallized from ethyl acetate to yield 80 mg of slightly impure product. This material was re-chromatographed on silica gel eluting with chloroform. The appropriate fractions were combined, the solvent evaporated, and the residue recrystallized from boiling diethyl ether, after addition of sufficient methylene chloride to effect complete dissolution, to yield 39 mg (24%) of pure product, m.p. 199°–201° C.

Anal. Calcd. for $C_{17}H_{18}N_2OS$: C, 68.42; H, 6.08; N, 9.39. Found: C, 68.82; H, 5.86; N, 9.32.

EXAMPLE 14

3-{[N-Phthalimidomethyl]amino}-5-ethyl-6-methyl-pyridin-2(1H)-one

To a suspension of 3-amino-5-ethyl-6-methylpyridin-2(1H)-one (73 mg, 0.48 mmol) in absolute ethanol (1.5 mL), under a nitrogen atmosphere, was added N-(hydroxymethyl)phthalimide (89 mg, 0.50 mmol). This mixture was refluxed for three hours during which complete dissolution of reagent occurred, followed by precipitation of the bright yellow product. Upon cooling, the precipitated product was collected by filtration and rinsed with ethanol and the diethyl ether to yield 130 mg (87%), m.p. 245°–247° C.

Anal. Calcd. for $C_{17}H_{17}N_3O_3$: C, 65.58; H, 5.51; N, 13.50. Found: C, 65.42; H, 5.52; N, 13.51.

EXAMPLE 15

3(2-Phthalimido ethyl)-5-ethyl-6-methylpyridin-2(1H)-one

Step A: Preparation of 2-methoxy-3-(2-amino-1-(R/S)-hydroxy ethyl)-5-ethyl-6-methylpyridine A mixture of 2-methoxy-5-ethyl-6-methylnicotinaldehyde (1.05 g, 5.86 mmol) and trimethylsilyl cyanide (0.85 mL, 6.37 mmol) containing zinc iodide (10 mg) was stirred, under a nitrogen atmosphere, at ambient temperature for two hours. This liquid was diluted with anhydrous diethyl ether, filtered and then added dropwise to a suspension of lithium aluminum hydride (225 mg, 5.9 mmol) in diethyl ether (15 mL) under nitrogen. After two hours the reaction was quenched with saturated aqueous sodium sulfate, diluted with methylene chloride, filtered and the solvents evaporated to give a semi-solid. This residue was triturated with cold diethyl ether and the crystalline product was collected by filtration to yield 346 mg (28%).

Step B: Preparation of 2-methoxy-3-(2-phthalimido-1-(R/S)-hydroxyethyl)-5-ethyl-6-methylpyridine To a suspension of 2-methoxy-3-(2-amino-1-(R/S)hydroxyethyl)-5-ethyl-6-methylpyridine (345 mg, 1.64 mmol) in ethanol (5 mL) was added N-(carbethoxy)-phthalimide (373 mg, 1.70 mmol). The reaction was stirred for six hours as suspension dissolved. The solvent was evaporated and the viscous residue triturated with ethyl acetate/diethyl ether as product crystallized. By filtration 273 mg (49%) of pure product was collected, m.p. 134°–135° C. These mother liquors were flash chromatographed on silica gel and eluted with 20% ethyl acetate/80% hexane to give an additional 83 mg (15%) of product.

Anal. calcd. for $C_{19}H_{20}N_2O_4$: C, 67.04; H, 5.92; N, 8.23. Found: C, 67.12; H, 5.92; N, 8.21.

Step C: Preparation of 3-(2-Phthalimido-ethenyl)-5-ethyl-6-methylpyridin-2(1H)-one A mixture of 2-methoxy-3-(2-amino-1(R/S)-hydroxyethyl)-5-ethyl-6-methylpyridine (172 mg, 0.50 mmol) and pyridine hydrochloride (600 mg, 5.3 mmol) was placed in a preheated oil bath at 150° C. for ten minutes. The mixture was cooled, diluted with water and the precipitated product collected by filtration and air dried to yield 145 mg (93%). Recrystallization from methanol gave analytically pure product m.p. 296°–298° C.

Anal. Calcd. for $C_{18}H_{16}N_2O_3$: C, 70.11; H, 5.23; N, 9.09. Found: C, 69.81; H, 4.99; N, 9.05.

Step D: Preparation of 3-(2-Phthalimido ethyl)-5-ethyl-6-methylpyridin-2(1H)-one A partial suspension of 3-(2-phthalimidoethenyl)-5-ethyl-6-methylpyridin-2(1H)-one (145 mg, 0.47 mmol) in methanol (20 mL) and tetrahydrofuran (20 mL) containing 5% palladium/carbon (117 mg) was hydrogenated at atmospheric pressure for 10–20 hours. The catalyst was filtered off and the solvents evaporated to give product. This material was recrystallized from methanol to yield 110 mg (75%), m.p. 232°–233° C.

Anal. Calcd. for $C_{18}H_{18}N_2O_3$: C, 69.66; H, 5.85; N, 9.03. Found: C, 69.44; H, 5.68; N, 8.98.

EXAMPLE 16

3-(2-Phthalimido ethyl)-5-ethyl-6-methyl pyridin-2(1H)-one

Step A: Preparation of 2-methoxy-3-(2-nitroethenyl)-5-ethyl-6-methylpyridine

A mixture of 2-methoxy-5-ethyl-6-methylnicotinaldehyde (2.25 g, 12.6 mmol), nitromethane (1.9 g, 31.1 mmol), monomethylamine hydrochloride (69 mg) and sodium hydroxide (20 mg) in absolute ethanol (1.3 mL) was stirred at ambient temperature for three days. This mixture was diluted with methanol and the precipitated yellow crystalline product was collected by filtration to yield 2.39 g (86%), m.p. 105°–107° C.

Step B: Preparation of 2-methoxy-3-(2-aminoethyl)-5-ethyl-6-methylpyridine

A suspension of 2-methoxy-3-(2-nitroethenyl)-5-ethyl-6-methylpyridine (445 mg, 2.0 mmol) in methanol (10 mL) and 4.7M methanolic hydrogen chloride (2 mL) containing 5% palladium/carbon (110 mg) was hydrogenated at atmospheric pressure over 10–20 hours. The catalyst was filtered off and the solvent evaporated. The residue was made basic with sodium hydroxide solution and the product extracted into methylene chloride, dried, filtered and the solvent evaporated to yield 332 mg of crude oily product. No further purification was performed.

Step C: Preparation of 2-methoxy-3-(2-phthalimidoethyl)-5-ethyl-6-methylpyridine To a solution of crude 2-methoxy-3-(2-aminoethyl)-5-ethyl-6-methylpyridine (332 mg) in ethanol (7 mL) was added N-(carbethoxy) phthalimide (406 mg, 1.85 mmol). After stirring at ambient temperature for three hours the solvent was evaporated and the residue was chromatographed on silica gel by gradient elution with 20–100% ethyl acetate/hexane. The appropriate fractions were combined, the solvent evaporated and the residue triturated with hexane as the product slowly crystallized out to yield 202 mg of pure product, m.p. 77°–79° C.

Anal. Calcd. for $C_{19}H_{20}N_2O_3$: C, 70.35; H, 6.22; N, 8.64. Found: C, 70.24; H, 6.10; N, 8.49.

Step D: Preparation of 3-(2-phthalimidoethyl)-5-ethyl-6-methylpyridin-2(1H)-one 2-methoxy-3-(2-phthalimidoethyl)-5-ethyl-6-methyl pyridine is heated at 150° C. for 5–10 minutes in the presence of excess pyridine hydrochloride to give the above titled product.

EXAMPLE 17

3-{[(N-Phthalimido)methyl]amino}-5-butyl-6-methyl-pyridin-2(1H)-one

Step A: Preparation of 3-cyano-5-butyl-6-methylpyridin-2(1H)-one

According to the method described in J. Heterocyclic Chem., 24, 351 (1987), a mixture of crude sodium 2-butyl-3-oxobutanal (7.39 g), cyanoacetamide (4.15 g, 39 mmol), aqueous piperidinum acetate (3.5 mL) [prepared from glacial acetic acid (0.85 ml), water (2.0 mL) and piperidine (1.45 ml)] in water (32 mL) was refluxed for 3 hours. Acetic acid (2.5 mL) was cautiously added. After cooling to room temperature and stirring overnight, the precipitated solids were collected by filtration. These residues (2.87 g) was chromatographed on silica gel by gradient elution with 1–3% methanol/ethyl acetate. The appropriate fractions were combined and evaporated. Crystallization from methanol gave 1.01 g of pure product.

Step B: Preparation of 5-butyl-6-methylpyridin-2(1H)-one

A suspension of 3-cyano-5-butyl-6-methylpyridin-2(1H)-one (950 mg, 5.0 mmol) in 6N hydrochloric acid (36 mL) was refluxed for 3 days. The reaction was cooled and extracted with methylene chloride to isolate product. It was then dried with methylene chloride solution, filtered and evaporated. The residue was triturated with diethyl ether to yield product (563 mg, 68%).

Step C: Preparation of 3-nitro-5-butyl-6-methylpyridin-2(1H)-one

A solution of 5-butyl-6-methylpyridin-2(1H)-one (562 mg, 3.40 mmol) in concentrated sulfuric acid (4.3 mL) was cooled in an ice bath and 70% nitric acid (0.4 mL) was added dropwise. After one hour, the reaction mixture was poured into ice/water and the yellow product extracted into methylene chloride. This solution was dried, filtered and evaporated. The residue (468 mg) was chromatographed on silica gel eluting with 1–2% methanol/chloroform to yield 293 mg (41%) of pure product.

Step D: Preparation of 3-amino-5-butyl-6-methylpyridin-2(1H)-one

A solution of 3-nitro-5-butyl-6-methylpyridin-2(1H)-one (293 mg, 1.40 mmol) in methanol (10 mL) and tetrahydrofuran (10 mL) containing 5% palladium/carbon (120 mg) was hydrogenated at atmosphere pressure for 10-20 hours. The catalyst was filtered off and the solvent evaporated. This residue was triturated with diethyl ether to give 224 mg (89%) of grayish product.

Step E: Preparation of 3-{[N-Phthalimidomethyl]-amino}-5-butyl-6-methylpyridin-2(1H)-one A mixture of 3-amino-5-butyl-6-methyl-2-pyridin-2(1H)-one (90 mg, 0.5 mmol) and N-(hydroxymethyl)phthalimide (143 mg, 0.8 mmol) in ethanol (3 mL) was refluxed for 7 hours. Upon cooling the product crystallized out and was filtered off to yield 125 mg (73%) of product. This material was crystallized from ethanol to give 52 mg of pure product, m.p. 209°-210° C.

Anal. Calcd. for $C_{19}H_{21}N_3O_3$: C, 67.24; H, 6.24; N, 12.38. Found: C, 66.98; H, 6.17; N, 12.12

EXAMPLE 18

Preparation of
3-[(2-Benzoxazolyl)methyl]amino-5-methylthio-6-methylpyridin-2(1H)-one and
3-[(Benzoxazolyl)methyl]amino-5-ethylthio-6-methylpyridin-2(1H)-one Step A: Preparation of 6-Methyl-5-methylthio-3-nitropyridin-2(1H)-one To a mixture of the sodium salt of 2-methylthio-3-oxo-1-butanal (1.54 g, 0.010 mol) and 2-nitroacetamide (1.10 g (0.0105 mol) in water (10 mL) was added aqueous 3.4M piperidinium acetate (0.71 mL). After stirring overnight at room temperature the yellow solids were removed by filtration, followed by washing with water. A yield of 0.874 g (43.65%) of analytically pure yellow solid, m.p. 199°-203° C. was obtained.

Anal. Calcd. for $C_7H_8N_2O_3S$: C, 41.99; H, 4.03, N, 13.99 Found: C, 41.82; H, 3.92; N, 14.00.

The corresponding 6-methyl-5-ethylthio-3-nitropyridin-2(1H)-one, prepared in a similar way, but starting with the sodium salt of 2-ethylthio-3-oxo-1-butanol had m.p. 190°-191° C. (Yield 43.6%).

Step B: Preparation of 3-[(2-Benzoxazolyl)methyl]-amino-5-methylthio-6-methylpyridin-2(1H)-one To a mixture of 5-methylthio-6-methyl-3-nitropyridin-2(1H)-one (0.60 g, 0.003 mmol) in MeOH (30 mL) at room temperature was added an aqueous solution of sodium hydrosulfite ($Na_2S_2O_4$) (1.74 g, 0.01 mol). When the yellow color disappeared after addition of additional sodium hydrosulfite (1.7 g), the reaction mixture was extracted with $CHCl_3$ (2×200 mL). The $CHCl_3$ extracts were washed with saturated aqueous $NaHCO_3$ solution, brine and then dried ($MgSO_4$). On concentration under vacuum there was obtained 0.20 g (39.4% yield) of 3-amino-5-methylthio-6-methylpyridin-2(1H)-one as a light yellow solid which was used without further purification.

A mixture of 3-amino-5-methylthio-6-methylpyridin-2(1H)-one (0.201 g, 0.0013 mol), 2-chloromethylbenzoxazole (0.239 g, 0.0014 mol), diisopropylethylamine (0.181 g, 0.0014 mol), and acetonitrile (6 mL) was heated at reflux under nitrogen for 35 hours. The dark solids which had formed were removed by filtration (0.089 g), and the filtrate evaporated to dryness. The two fractions were combined and chromatographed on a 30 mm column containing 230-400 mesh silica gel (6 inches). The column was prepared with methylene chloride and the crude product applied in methylene chloride. Development of the column was with 2% 2-propanol/methylene chloride (500 mL), 5% 2-propanol/methylene chloride (500 mL), and 10% 2-propanol/methylene chloride (1000 mL). Concentration of the fractions containing the desired product gave 0.133 g (33.5% yield) of 3-[(2-Benzoxazolyl)methyl]-amino-5-methylthio-6-methylpyridin-2(1H)-one m.p. 180°-181° C.

Anal. Calcd for $C_{15}H_{15}N_3O_2S \cdot 0.2H_2O$ C, 59.08; H, 5.09; N, 13.78. Found: C, 59.27; H, 5.03; N, 13.75.

The corresponding 5-ethylthio analog was prepared in the same way except that the bis-1,8-dimethylaminonaphthalene was used as base in the alkylation step; m.p. 197°-200° C., (34.9% yield).

Anal. Calcd for $C_{16}H_{17}N_3O_2S$: C, 60.93; H, 5.43; N, 13.32. Found: C, 60.95; H, 5.46; N, 13.26.

EXAMPLE 19

Preparation of
3-[2-(4,7-dichlorobenzoxazolyl)methyl]-amino-5-ethyl-6-methyl-1H-pyridin-2-one Step A: Preparation of 2-amino-3,6-dichlorophenol A yellow solution of 2,5-dichloro-6-nitrophenol (10.0 g, 48.0 mmol) in ethanol (200 mL) and acetic acid (13.8 mL) at 0° C. was catalytically reduced in the presence of 5% Platinum on charcoal (0.15 g) under an atmosphere of hydrogen (25 psi) for 1 hour in a Parr hydrogenator. The resultant colorless solution was filtered and concentrated under reduced pressure (15 torr). The residue was then dried under high vacuum (0.02 torr) overnight to yield 8.52 g (100%) of 2-amino-3,6-dichlorophenol.

Step B: Preparation of 2-chloromethyl-4,7-dichlorobenzoxazole

To a solution of 2-amino-3,6-dichlorophenol (23.91 g, 134 mmol) in methylene chloride (270 mL), solid ethyl chloroiminoacetate hydrogen chloride (31.9 g, 202 mmol) was added. The resultant slurry was stirred at room temperature overnight, then filtered through a plug of Celite, and concentrated under reduced pressure (15 torr). The solid residue was subjected to column chromatography on silica gel (elution with chloroform). Collection and concentration of appropriate fractions yielded 26.6 g (86%) of 2-chloromethyl-4,7-dichlorobenzoxazole.

Step C: Preparation of 3-[2-(4,7-dichlorobenzoxazolyl)-methyl]amino-5-ethyl-6-methyl-1H-pyridin-2-one A mixture of 3-amino-5-ethyl-6-methylpyridine-2-one (0.93 g, 6.1 mmol), 2-chloromethyl-4,7-dichlorobenzoxazole (1.45 g, 6.1 mmol), diisopropylethylamine (1.06 mL, 6.1 mmol) in acetonitrile (30 mL) was refluxed under an atmosphere of nitrogen for 20 hours. The resultant mixture was cooled to 0° C. The solid precipitated was filtered and subjected to column chromatography on silica gel (elution with 4% methanol in chloroform). Collection and concentration of appropriate fractions provided 0.76 g of a white solid which was then recrystallized from ethanol to yield 0.66 g (31%) of 3-[2-(4,7-dichlorobenzoxazolyl)methyl]amino-5-ethyl-6-methyl-1H-pyridinone. Anal. Calcd for $C_{16}H_{15}Cl_2N_3O_2$: C, 54.56; H, 4.29; N, 11.93. Found: C, 54.43; H, 4.12; N, 11.89.

Reverse Transcriptase Assay

The assay measures the incorporation of tritiated deoxyguanosine monophosphate by recombinant HIV reverse transcriptase (HIV $RT_R$) (or other RT) into acid-precipitable cDNA at the Km values of dGTP and poly r(C)•oligo d(G)$_{12-18}$. The inhibitors of the present invention inhibit this incorporation.

Thirty uL of a reaction mixture containing equal volumes of: 500 mM Tris•HCl (pH 8.2), 300 mM MgCl$_2$, 1200 mM KCl, 10 mM DTT, 400 μg/mL poly r(c)•oligo d(G) [prepared by dissolving 1.5 mg (25 U) poly r(C)•oligo d(G) in 1.5 ml sterile distilled H$_2$O and diluting to 400 μg/ml], 0.1 μCi/μl ]$^3$H] dGTP, 160 μM dGTP, was added to 10 μl sterile distilled H$_2$O, 2.5 μl of potential inhibitor and 10 μL of 5 nM purified HIV $RT_R$ in tubes. The mixture was incubated at 37° C. for 45 minutes.

After incubation is complete, the tubes were cooled in ice for 5 minutes. Ice-cold 13% TCA containing 10 mM NaPP$_i$ (200 μl) are added and the mixture incubated on ice for 30 minutes. The precipitated cDNA is removed by filtration using presoaked glass filters [TCA, NaPP$_i$]. The precipitate is then washed with 1N HCl, 10 mM NaPP$_i$.

The filter discs are then counted in a scintillation counter.

Under these conditions [dGTP] and poly r(C)•oligo d(G)$_{12-18}$ each are approximately equal to the appropriate Km value. Approximately 5-6,000 cpm of [$^3$H] GMP are incorporated into acid-precipitable material. The RT reaction is concentration- and time-dependent. DMSO (up to 5%) does not affect enzyme activity. Calculated IC$_{50}$ values for the compounds of this invention vary from about 10 nM to more than 300 μM.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A compound of the formula:

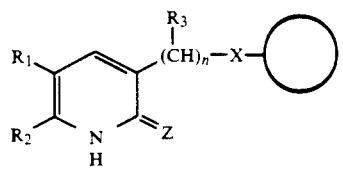

wherein:
X is NH, O, or S;
Z is O or S;
n is 1–4;
R$_1$ is
(i) C$_{1-8}$ alkyl, unsubstituted or substituted with one or two of C$_{1-3}$alkoxy, halo, C$_{1-4}$alkylamino, C$_{1-4}$-di-alkylamino, or C$_{1-3}$ alkylthio;
(ii) C$_{1-3}$ alkylthio;
(iii) C$_{1-3}$ alkoxy; or
(iv) halo;
R$_2$ is H, methyl or ethyl, unsubstituted or substituted with one or two of methoxy, methylamino, dimethylamino or methylthio;
R$_3$ is H or C$_{1-8}$ alkyl;
—◯ is 2-benzoxazolyl, unsubstituted or substituted with one or more of methyl, halogen or hydroxyl.

2. A compound of claim 1, wherein 2-benzoxazolyl is unsubstituted, or substituted as 7-methyl-2-benzoxazolyl, 4,7-dimethyl-2-benzoxazolyl, 7-chloro-2-benzoxazolyl, or 4,7-dichloro-2-benzoxazolyl.

3. A pharmaceutical composition useful for inhibiting HIV reverse transcriptase, comprising an effective amount of a compound as in any of claims 1 or 2, and a pharmaceutically acceptable carrier.

4. A pharmaceutical composition useful for preventing or treating infection of HIV or for teating AIDS or ARC, comprising an effective amount of a compound as in any of claims 1 or 2, and a pharmaceutically acceptable carrier.

* * * * *